United States Patent

Chernoff

[11] Patent Number: 6,135,994
[45] Date of Patent: Oct. 24, 2000

[54] SURGICAL METHOD

[76] Inventor: W. Gregory Chernoff, 5846 N. LaSalle St., Indianapolis, Ind. 46220

[21] Appl. No.: 08/945,068

[22] PCT Filed: Apr. 17, 1996

[86] PCT No.: PCT/US96/05286

§ 371 Date: Dec. 18, 1997

§ 102(e) Date: Dec. 18, 1997

[87] PCT Pub. No.: WO96/32886

PCT Pub. Date: Oct. 24, 1996

Related U.S. Application Data

[63] Continuation-in-part of application No. 08/423,038, Apr. 17, 1995.

[51] Int. Cl.[7] .................................................. A61B 17/36
[52] U.S. Cl. .................................. 606/9; 606/10; 606/12
[58] Field of Search ................................. 606/10, 11, 12, 606/14, 15, 16, 17

[56] References Cited

U.S. PATENT DOCUMENTS 4,973,848  11/1990  Kolobanov et al. .
5,254,112  10/1993  Sinofsky et al. .
5,464,013  11/1995  Lemelson .................................. 606/10

OTHER PUBLICATIONS

"IEEE 1989 Ultrasonics Symposium Proceedings," sponsored by the Ultrasonics Ferroelectric and Frequency Control Society, Oct. 3–6, 1989, Le Grand Hotel, Montréal, Québec, Canada; B. R. McAvoy, Editor.

*Primary Examiner*—Linda C. M. Dvorak
*Assistant Examiner*—Sonya Harris-Ogugua
*Attorney, Agent, or Firm*—Barnes & Thornburg

[57] ABSTRACT

A surgical method comprises successively orienting an ultrasound transmitter (30) to transmit ultrasound from multiple locations (65) adjacent the skin (32) surface and at each of the multiple locations (65) transmitting ultrasound (30), generating a time base, receiving ultrasound echoes, and determining from the time between transmission and reception the depth beneath the skin of tissue to be treated. The depths of the tissue (36) at the multiple locations are stored in a memory (40) associated with a programmable machine (34). The laser (50) is successively targeted on each of the multiple locations (65), and at each of the multiple locations (65) the depth of the tissue (36) to be treated beneath that location (65) is retrieved from the memory (40). The retrieved depth of the tissue (36) to be treated beneath that location determines a laser (50) excitation power that will achieve treatment of the tissue (36) at the retrieved depth. The laser (50) is excited at the determined excitation power.

12 Claims, 11 Drawing Sheets

SURGICAL METHOD

CROSS-REFERENCES TO RELATED APPLICATIONS

This application is a U.S. national application of international application Ser. No. PCT/US96/05286 filed Apr. 17, 1996, which is a continuation-in-part of U.S. Ser. No. 08/423,038 filed Apr. 17, 1995.

TECHNICAL FIELD AND INDUSTRIAL APPLICABILITY

This invention is disclosed in the context of cosmetic and reconstructive surgical procedures. However, it is believed to be useful in other applications as well.

BACKGROUND ART

Various techniques for facial cosmetic and reconstructive surgery are known. There are, for example, the techniques known as chemical peels and dermabrasion. More recently, laser cosmetic surgical techniques have become of interest. This recent interest parallels the development of small, highly maneuverable laser handpieces. Examples of these types of equipment are the SilkTouch™ model laser available from Sharplan Lasers, Inc., One Pearl Court, Allendale, N.J. 07401 and the UltraPulse™ model laser available from Coherent, Inc., 3270 West Bayshore Road, Palo Alto, Calif. 94303-4043.

Characterization of dermal structure by ultrasound is also known. There is, for example, *Aging Skin Properties and Functional Changes,* eds. Lévêque, Jean-Luc and Pierre G. Agache. Chapter 7 of this reference describes high frequency ultrasound characterization of skin.

Computer imaging is presently in use in pre-operative surgical evaluations. There is, for example, the Mirror II aesthetic imaging system available from Mirror Image Technology, 4300 198th Street SW, Suite 200, Lynnwood, Wash. 98036. These systems can be thought of as dividing patient images digitized from color camera output into pixels and storing them as, for example, color and intensity information, pixel by pixel. Imaging of cosmetic and reconstructive surgical results can then be obtained by various types of averaging of stored intensity and color value data over numbers of adjacent pixels selected, for example, interactively by the physician and/or physician's assistant in consultation with the patient. This provides the patient with realistic expectations of various surgical outcomes prospectively, so that more informed elective decisions can be made.

DISCLOSURE OF INVENTION

According to the invention, a surgical method comprises orienting an ultrasound transmitter to transmit ultrasound from a first location on the skin surface, transmitting the ultrasound, generating a time base, receiving ultrasound echoes, and determining from the time between transmission and reception the depth beneath the skin of tissue to be treated. The ultrasound transmitter is then successively oriented to transmit ultrasound from multiple additional locations. At each of the multiple additional locations, the ultrasound is transmitted, a time base is generated, ultrasound echoes are received, and the depth beneath the skin of tissue to be treated is determined from the time between transmission and reception. The depths of the tissue at the first location and the multiple additional locations are stored in a memory associated with a process controller. A laser is targeted on the first location. The depth of the tissue to be treated beneath the first location is retrieved from the memory. A laser excitation power that will achieve treatment of the tissue at the retrieved depth is calculated from the retrieved depth of the tissue to be treated beneath the first location. The laser is excited at this power. The laser is successively targeted on each of the multiple additional locations, and at each of the multiple additional locations the depth of the tissue to be treated beneath that said location is retrieved from the memory. A laser excitation power that will achieve treatment of the tissue at the retrieved depth is calculated from the retrieved depth of the tissue to be treated beneath that said location. The laser is excited at each of these powers.

Illustratively according to the invention, the steps of determining from the time between transmission and reception the depth beneath the skin surface of tissue to be treated comprise the steps of determining from the time between transmission and reception the depth beneath the skin surface of the reticular dermis.

Alternatively, illustratively according to the invention, the steps of determining from the time between transmission and reception the depth beneath the skin surface of tissue to be treated comprise the steps of determining from the time between transmission and reception the depth beneath the skin surface of the papillary dermis.

The invention may best be understood by referring to the following detailed description and accompanying drawings which illustrate the invention. In the drawings:

MODES FOR CARRYING OUT THE INVENTION

Figure 1:
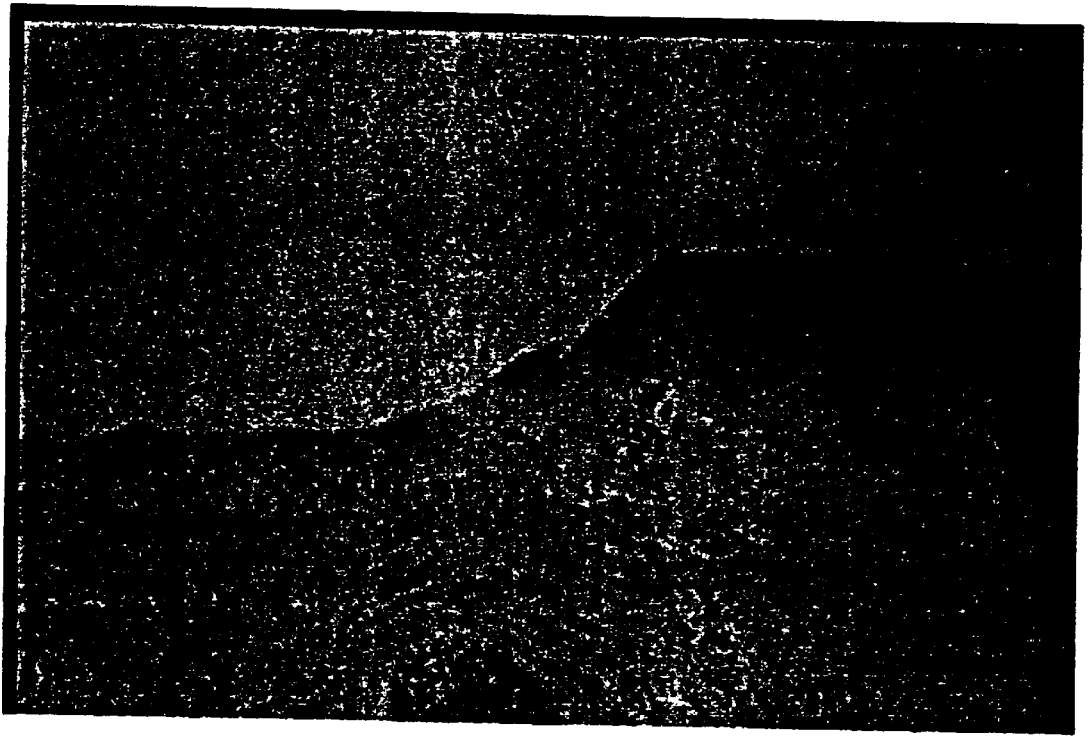
FIG. 1 illustrates a histology resulting from treatment with a Sharplan laser with a setting of 7 watts, an exposure time of 0.2 second, and a single pass or exposure of the tissue to the laser.
Figure 2:
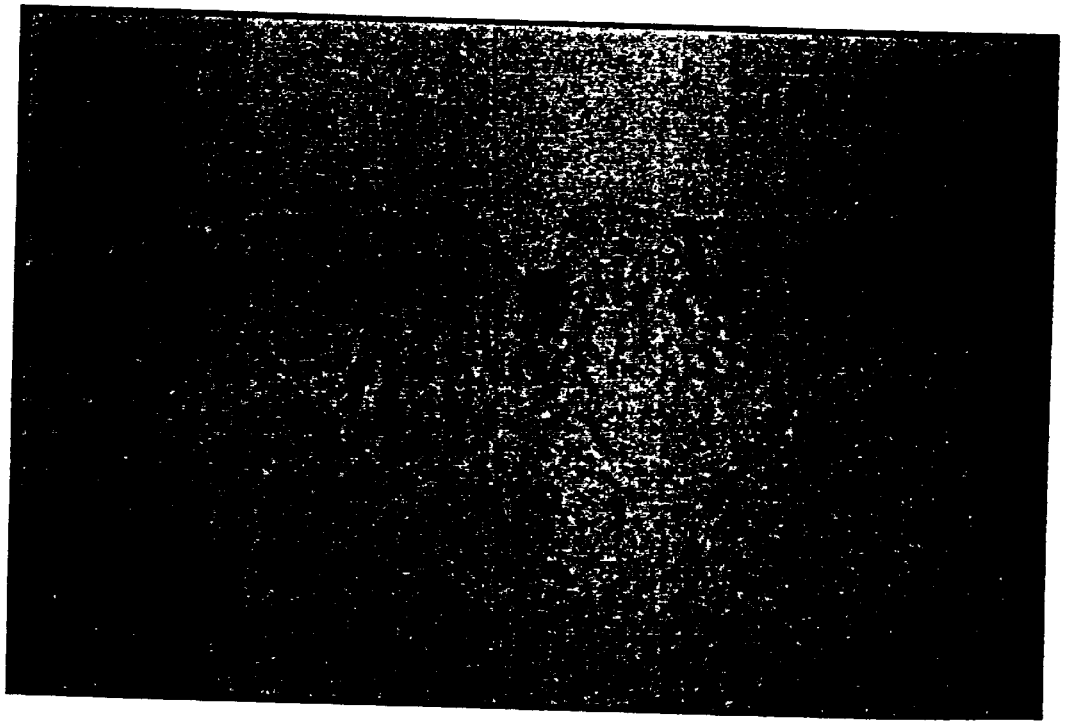
FIG. 2 illustrates a histology resulting from treatment with a Sharplan laser with a setting of 7 watts, an exposure time of 0.2 second, and a single pass.
Figure 3:
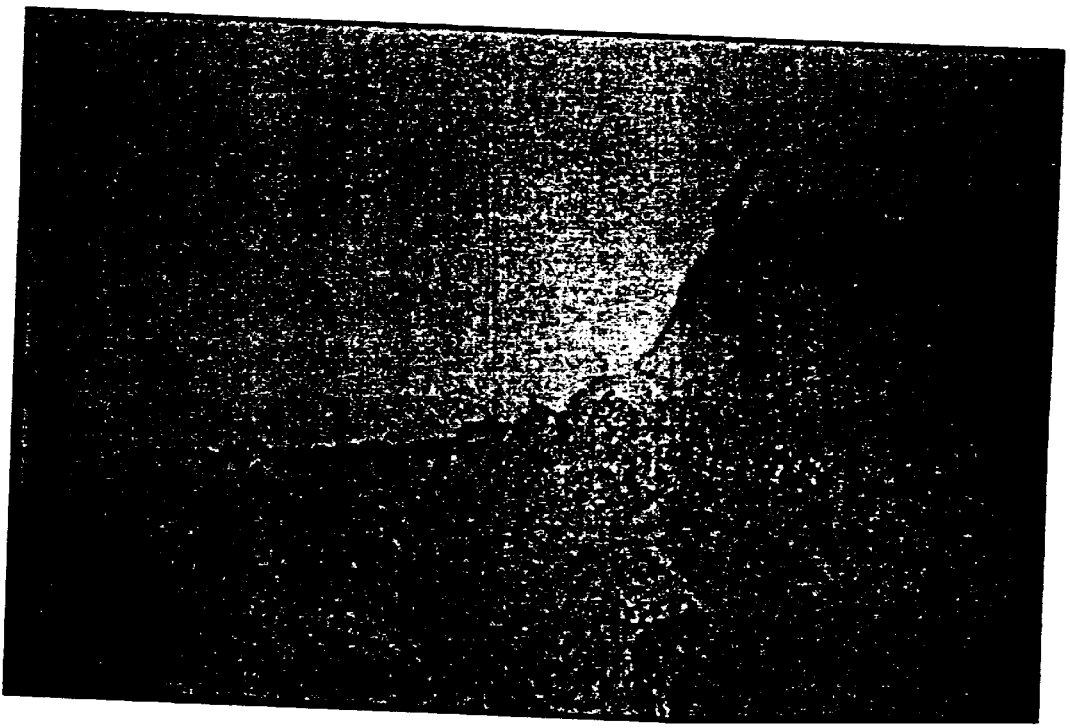
FIG. 3 illustrates a histology resulting from treatment with a Sharplan laser with a setting of 7.5 watts, exposure time of 0.2 second per pass, and two passes.
Figure 4:
FIG. 4 illustrates a histology resulting from treatment with a Sharplan laser with a setting of 8 watts, exposure times of 0.2 second per pass, and two passes.
Figure 5:
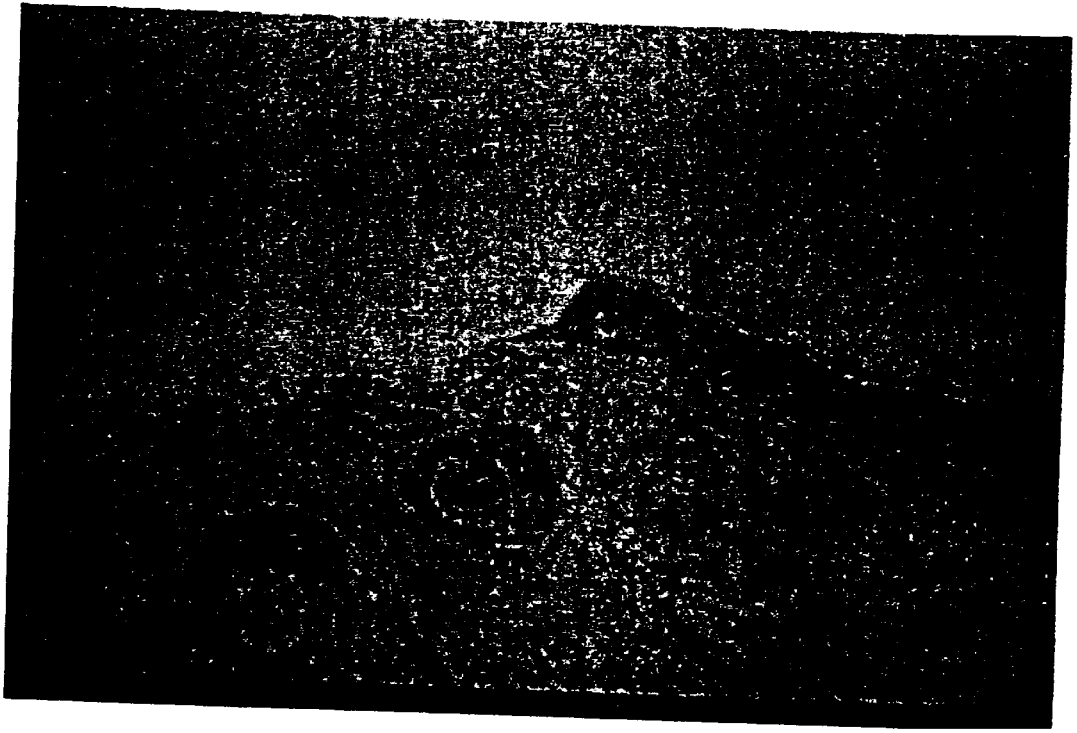
FIG. 5 illustrates a histology resulting from treatment with a Coherent laser with a setting of 250 mJ/3 watts and a single pass.
Figure 6:
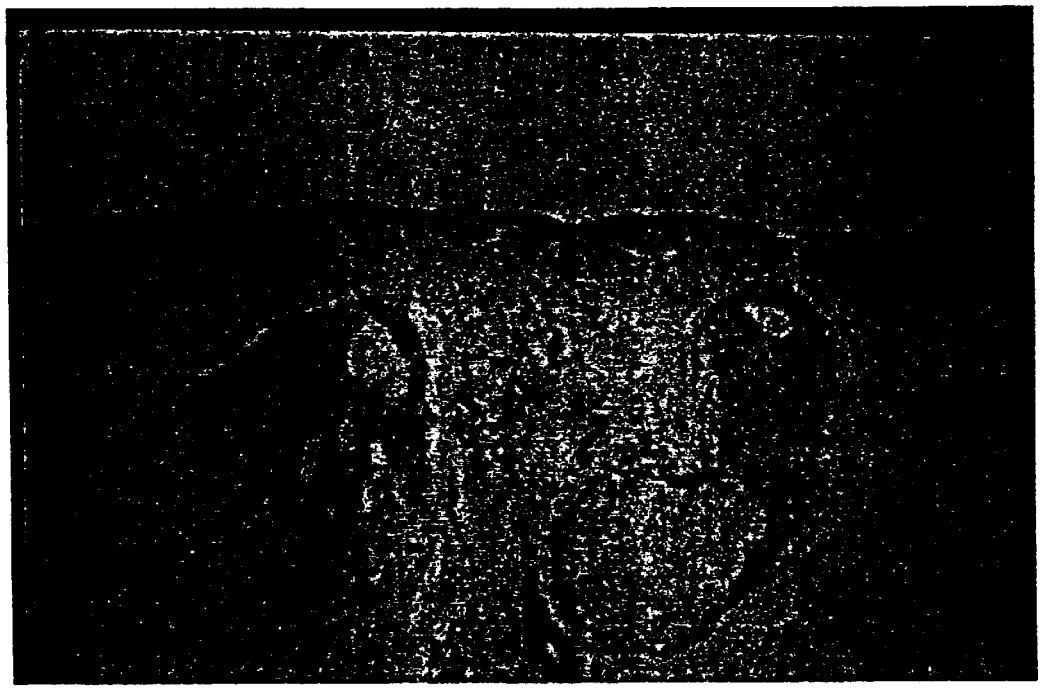
FIG. 6 illustrates a histology resulting from treatment with a Coherent laser with a setting of 250 mJ/4 watts and a single pass.
Figure 7:
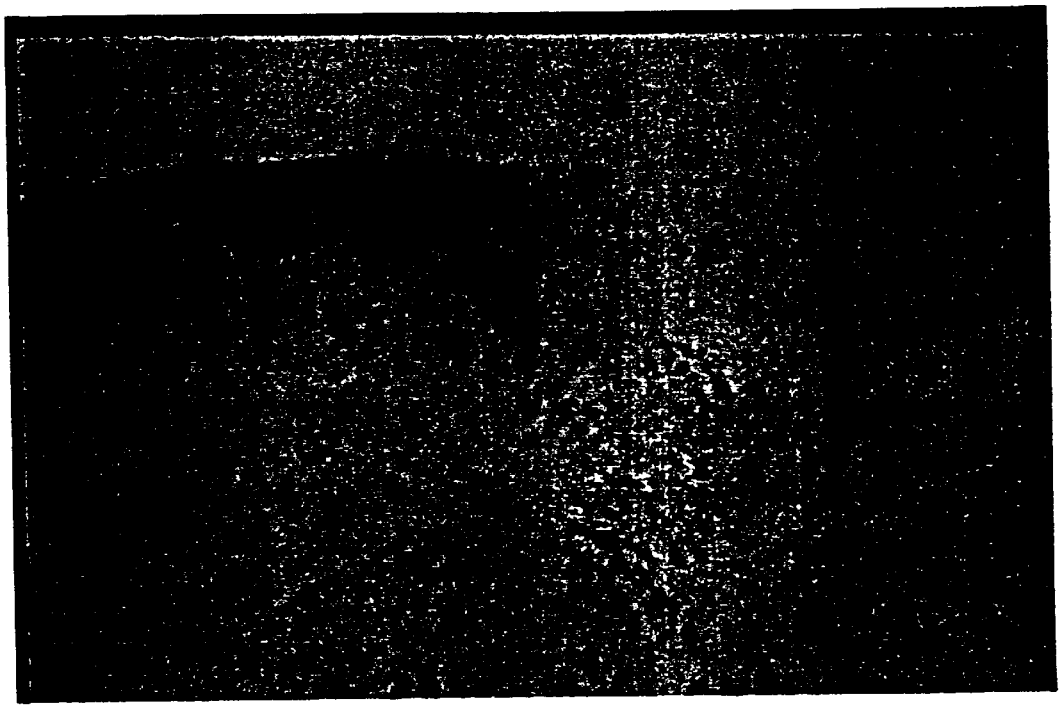
FIG. 7 illustrates a histology resulting from treatment with a Coherent laser with a setting of 450 mJ/3 watts per pass and two passes.
Figure 8:
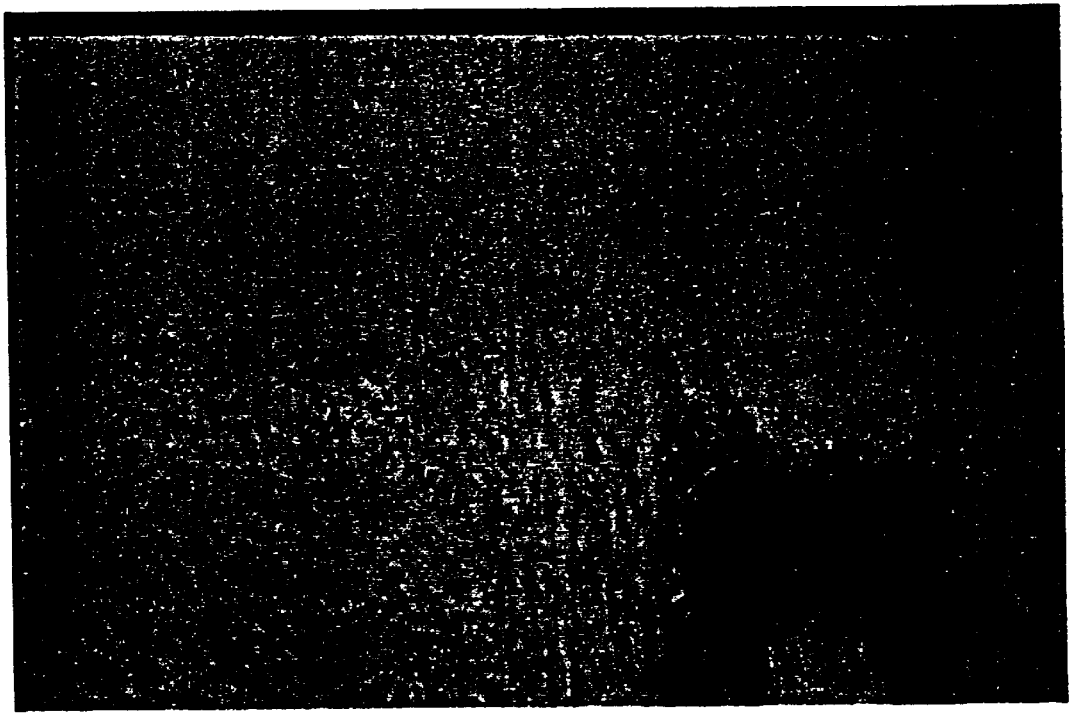
FIG. 8 illustrates a histology resulting from treatment with a Coherent laser with a setting of 450 mJ/3 watts per pass and two passes.
Figure 9:
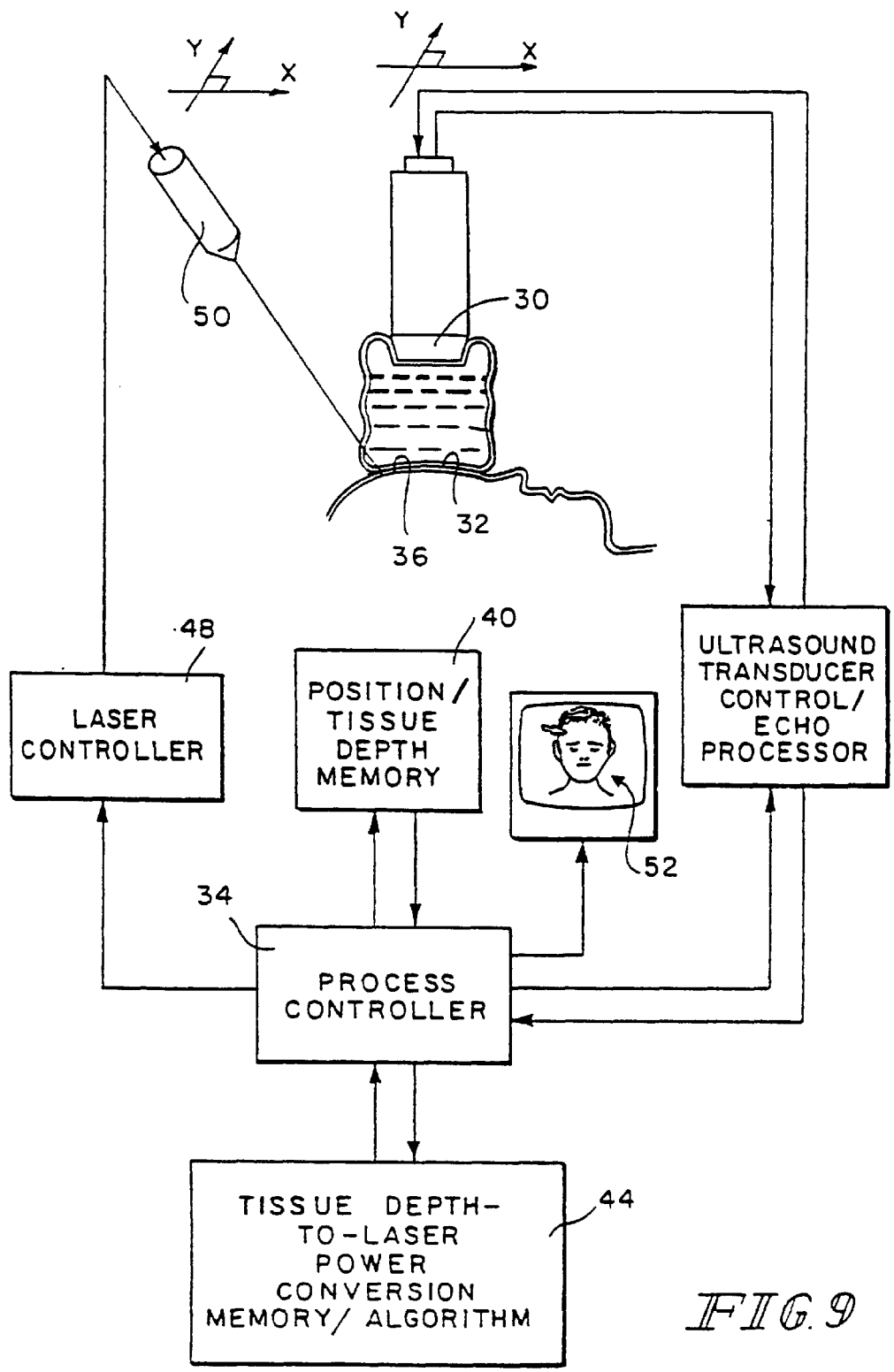
FIG. 9 illustrates a simplified block diagram of a system constructed according to the present invention.

The inventor has characterized the laser power required to effect desired cosmetic and reconstructive surgical results.

This power varies with tissue thickness which varies: over the surgical field; by skin type, for example, Fitzpatrick skin type; facial types; and, facial textures, among other things.

Patients ranged in age from thirty-four to seventy-eight years of age. Untreated skin of the same patient served as a control in each case. Skin from all facial zones was treated. The patient population encompassed all Fitzpatrick skin types including all combinations of possible texture variations. These included skin affected by chronological aging, photo-aging, rhytids classified as fine, moderate and deep, and linear, acne and pox scars. Pathologists examined histological specimens and graded the specimens according to specific, defined criteria. Four hundred ninety-eight histological specimens were examined by two pathologists who were blinded to the experiment.

Both of the previously identified Coherent and Sharplan lasers were evaluated. A focusing handpiece of 125 mm focal length was used with the Sharplan laser. The Sharplan laser generates a focal spot which scans spirally, covering a generally circular area. Operating parameters were chosen to provide selectable treatment spirals having 2.0, 2.5 and 3.0 mm diameters. The movement of the beam over the tissue ensured a 1.0 millisecond exposure duration on individual sites within the area, resulting in very shallow ablation.

The actual beam diameter in the focal plane (in the tissue) was smaller than 0.20 mm. A power level of 7.0 watts generated an optical power density of above 100 W/mm$^2$ on the tissue. This is above the threshold for tissue vaporization without carbon residue (about 50 W/mm$^2$). The time required for the Sharplan laser to trace its 2.0 mm–to –3.0 mm diameter spiral pattern was about 200 milliseconds. During this time, the 7 watt power level delivered 1400 mJ of heat to the tissue. Minimal subcrater thermal reaction was achieved by delivering the energy required for tissue ablation in pulses of shorter duration than the thermal relaxation time of the tissue.

The above-identified Coherent laser incorporated radio-frequency gas-slab technology, permitting tissue to be vaporized in times shorter than that required to induce appreciable heat conduction into surrounding tissue. Thermal damage to the surrounding tissue was thereby avoided. The power density delivered during a single laser pulse is above the threshold needed for tissue vaporization without appreciable carbon residue. Consequently, the rate of vaporization is faster than the rate of heat conduction.

Of the total number of pathological specimens reviewed by the pathologists, 276 specimens were treated using the Sharplan system and 222 were treated using the Coherent system. All combinations of laser power settings, skin type, facial zones and scar types were investigated.

Several factors were found to affect exfoliation. These factors highlight the importance of achieving a balance between adequate depth of treatment and avoiding thermal damage to the remaining tissue. Optimal clinical benefit of the procedure as it relates to rhytids, scars and skin texture equates with reaching exfoliation depths in the papillary dermis to the reticular dermis. The ideal laser ablation scenario involves reaching this level with the least number of treatment passes and the smallest amount of thermal reaction in the adjacent tissue. However, based upon the tissue thickness overlying the reticular dermis, it is not always possible to reach the reticular dermis with one pass without causing significant thermal damage. Thermal reaction in acceptable exfoliated specimens was found to be in the range of 30–50 microns, regardless of the laser system employed.

The surgeon must constantly be aware of what tissue depth has been reached with each pass of the laser. This can be determined visually from the color of the tissue displayed to the physician when the treated, exfoliated debris is removed. A pink tone denotes that only the epidermis has been treated. A grey tinge indicates that the papillary dermis has been exposed. A chamois-yellow color denotes that the reticular dermis has been exposed.

FIGS. 1–4 illustrate histologies resulting with settings and passes with the Sharplan system yielding acceptable exfoliation results. FIGS. 5–8 illustrate histologies with the Coherent system and yielding acceptable exfoliation results.

Upon completion of the histological analysis, parameter setting were determined for the Sharplan and Coherent systems which gave consistently acceptable results per pass with regard to acceptable levels of thermal reaction in adjacent tissue. These parameter settings varied with skin type, epidermal thickness, dermal thickness, lesion type, facial zone and previous exfoliation history. While there is not a direct correlation between tween Fitzpatrick skin types and epidermal and dermal thickness, Fitzpatrick skin types can serve as a guide of relative values when initiating laser therapy and choosing safe starting parameters. It should be understood, however, that a Fitzpatrick skin type 1 patient may have a thicker epidermis/dermis than a Fitzpatrick skin type 4 patient, depending on aging characteristics. Table 1 delineates safe treatment starting parameters for each system.

TABLE 1

TREATMENT STARTING PARAMETERS

| Fitzpatrick Skin Type | Sharplan Laser Settings (watts- 125 mm focal length handpiece (+) spot size) | Coherent Laser Settings (millijoules/watts- 0 mm handpiece) |
| --- | --- | --- |
| 1 | 5.5–6.5 | 250/2 |
| 2 | 5.5–6.5 | 250/2 |
| 3 | 7.0–7.5 | 300/2–3 |
| 4 | 7.0–7.5 | 300/2–3 |
| 5 | 7.5–8.0 | 350–450/2–4 |
| 6 | 7.5–8.0 | 350–450/2–4 |

Review of the histological specimens revealed several factors. First, consistent acceptable results can only be achieved through practice of the described method. Selective, precise depth control which is reproducible within facial zones and from patient to patient is possible with practice. Accurate linear control, leading to less pigment variation, is achievable with this exfoliation method. Cutaneous laser exfoliation with minimum thermal reaction to the remaining dermis is possible. Minimal trauma to remaining adnexal structures ensures adequate healing.

After reviewing the pathological data, the laser settings specific to the above-noted factors found to affect laser resurfacing, were defined and refined. These settings are provided in Table 2.

TABLE 2

FACTORS AFFECTING LASER RESURFACING

| FACTOR | SHARPLAN | COHERENT |
| --- | --- | --- |
| Thin Epidermis | reduce watts by 10% | reduce millijoules by 10% |

TABLE 2-continued

FACTORS AFFECTING LASER RESURFACING

| FACTOR | SHARPLAN | COHERENT |
|---|---|---|
| Scars | increase watts by 10% | increase millijoules by 10% |
| Reduced Spot Size | reduce power in proportion to reduction in spot area | N/A |
| Starting Power | 7.0 watts | 250 millijoules/2–3 watts |
| Linear Method | Lesion Facial Zone | Lesion Facial Zone |
| Avoid Overlap | Yes | Yes |
| Saline Wipe Exfoliant | Yes | Yes |

Once reproducibility was demonstrated and established, twenty-five patients (21 female, 4 male) were examined. The patients' ages ranged from 41 to 78 years, with a mean of 57 years. All skin types were represented as were each of the facial zones, rhytid types and scar types. Patient tolerance to the procedure utilizing a range of anesthetics from topical to injectable was examined. The benefits of oral corticosteroids and occlusive ointments and dressings were also examined. These studies have yielded encouraging results demonstrating the efficacy of the described resurfacing techniques. These demonstrate that cutaneous laser resurfacing offers an alternative to conventional exfoliation methods. Taking into account skin variation between patients as well as interzonal variations within each patient, the inventive technique permits selective, precise, depth-controlled exfoliation with minimal thermal disruption to adjacent tissue. The described studies demonstrate the reproducibility and acceptability of the clinical results available with the inventive technique.

This technique is believed to have broad applicability. It is not intended to replace chemical or mechanical treatments. For example, combinations of conventional therapies with laser resurfacing may be indicated. The combination of laser resurfacing and tissue augmentation may also prove valuable in the treatment armamentarium as well.

Several multicentered studies geared towards improving delivery systems and methods of acceleration post-treatment healing are currently in progress. Of course, techniques can only be adopted and implemented with reasoned, thorough clinical judgment as to patient safety. Adequate training in laser safety and procedure are essential before the physician embarks upon laser resurfacing within his or her practice.

According to an illustrative embodiment of the invention, an ultrasound transducer 30 is provided. The transducer 30 can be on an x-y drive to traverse a surface 32 under the control of a process controller 34. Alternatively, transducer 30 can have a process controller 34—controllable focal point which effectively scans the surface 32 electrically rather than mechanically. Such devices are known. There are, for example, the devices illustrated and described in U.S. Pat. Nos.: 4,084,582; 4,207,901; 4,223,560; 4,227,417; 4,248,090; 4,257,271; 4,317,370; 4,325,381; and, 4,664,121 and referenced cited therein. No representation is intended, nor should any such representation be inferred, that a thorough search of all pertinent prior art has been conducted, or that the above-identified patents constitute the best available prior art.

In any event, as the scan proceeds, depths of a tissue layer 36 to be treated, for example, the reticular dermis, beneath the surface 32 are ascertained from the received ultrasound echoes in accordance with the teachings of the above-referenced *Aging Skin Properties and Functional Changes*. These depths are correlated with their locations in the scan and stored in a scan position/tissue depth memory 40 in the system. Either as the ultrasound tissue depth mapping scan proceeds or after this scan has been completed, the tissue depths corresponding to the various positions or "addresses" of the ultrasound scan are compared to the laser power values in a tissue depth-to-laser power lookup table 44. Alternatively, an algorithm for determining the appropriate laser power setting from the echo-derived treatment depth can be used to establish the laser power setting. In any event, the laser powers necessary to achieve the appropriate degrees of exfoliation for a particular laser pass are established and are used to control the power supplied by a laser controller 48 to a laser emitter 50. Illustrative laser emitters 50 are the handpieces of the above-identified Sharplan and Coherent lasers. If the ultrasound transducer 30 and/or the laser emitter 50 is/are manually guided, a video display 52 of the appropriate target location on surface 32 can be provided to direct the medical service provider to the correct address. Alternatively, the focal spot of the emitter 50 could be mechanically controlled by an x-y motion drive to orient the emitter 50 properly over the various addresses whose tissue depths are being called up, as those addresses and tissue depths are being called up, to provide the power to achieve the appropriate degree of exfoliation in the laser 50 pass being conducted.

Figure 10:
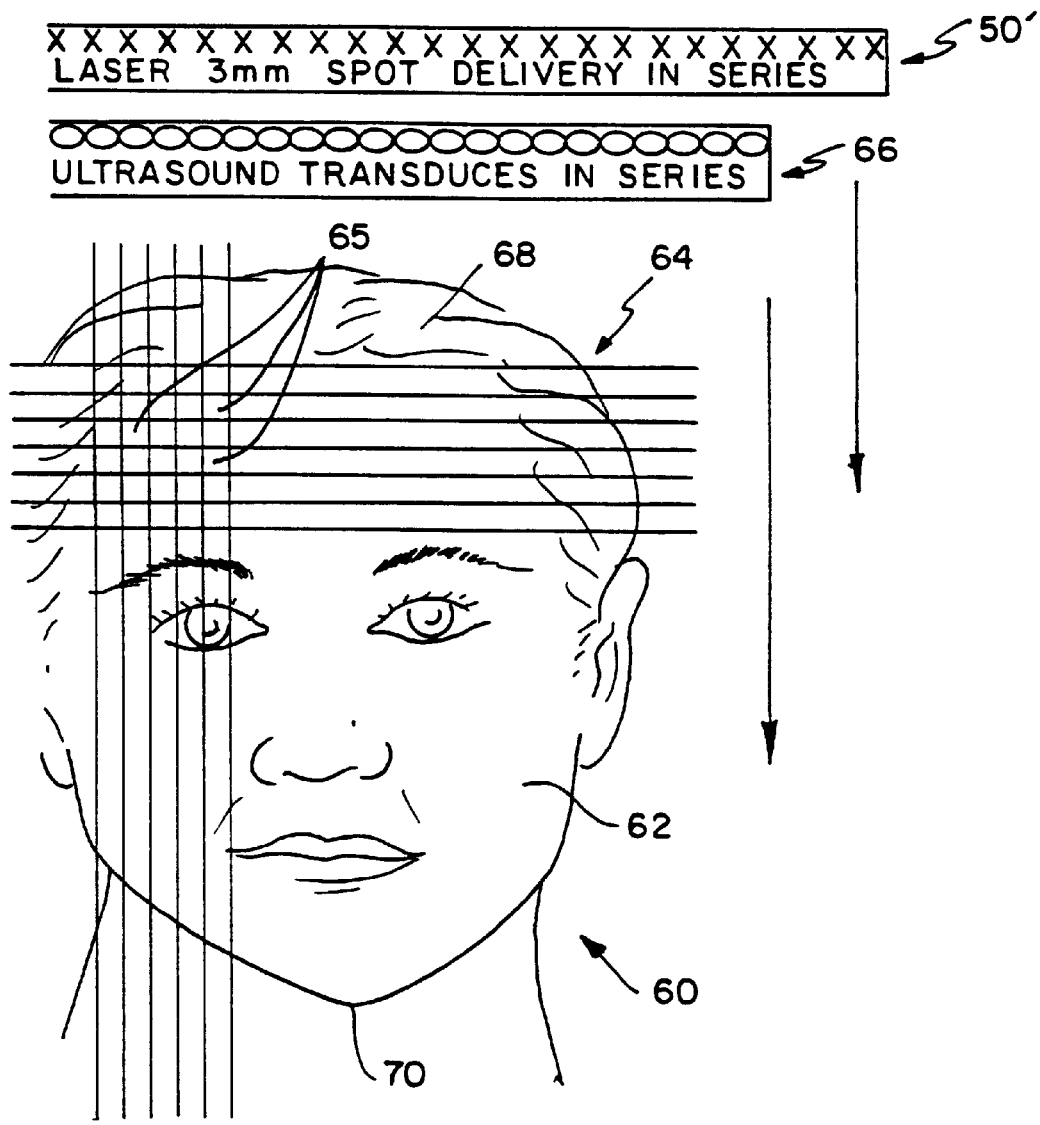
FIGS. 10–11 illustrate front and right side views of face, respectively, illustrating the use of the present invention.
Figure 11:
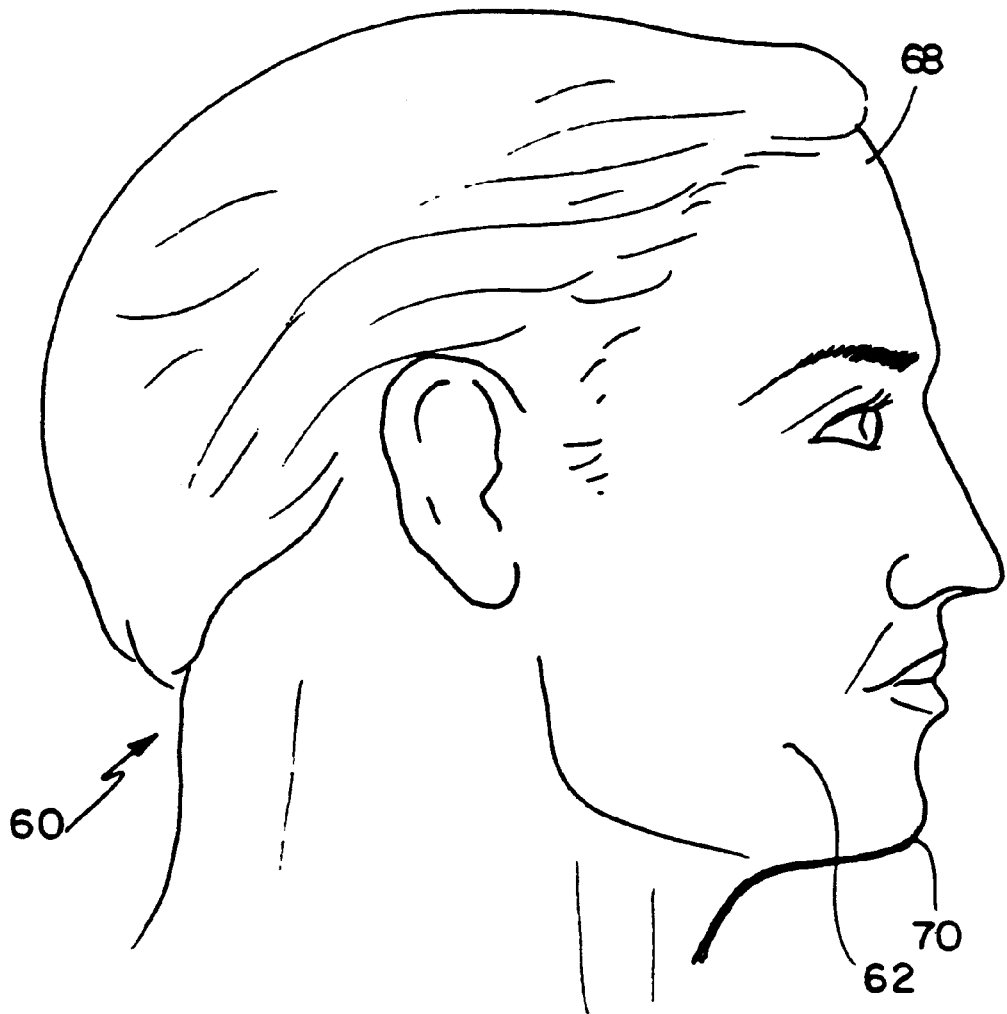

With reference to FIGS. 10–11, patient 60 treatment would proceed along the following lines: the patient 60 is imaged on the above-identified Mirror II aesthetic imaging system, capturing the patient's face 62 within a digital grid 64, only a portion of which is illustrated, of the computer associated with the aesthetic imaging system. The patient 60 is then considered in connection with the x-y coordinates of each pixel, or of an arbitrarily large or small group of neighboring pixels 65, within the digital image of the face 62. An ultrasound transducer 30 of the type described in any of the above-identified patents, or a linear array of such transducers 66 is indexed across the face 62, for example, from forehead 68 to chin 70 or from chin 70 to forehead 68, recording the depth to the reticular dermis 36 within each pixel or group of neighboring pixels 65 of the patient's face 62 as captured in the digital grid 64. The process controller 34 of the system stores the tissue 36 depths with their respective locations on the grid 64. It then relays this depth information to the laser orienting system and to the laser power controller 48 which then controls the laser 50, or a linear array of 50' of, for example, 3 mm spot delivery lasers 50, both in terms of its focal point and power to expose the points on the grid 64 to appropriate power level laser exposure to achieve treatment of the reticular dermis 36.

We claim:

1. An apparatus comprising an ultrasound transducer, a coupler for coupling ultrasound emitted by the transducer to the surface of the skin of a patient, the transducer receiving echoes from the patient's skin and structure beneath the patient's skin, a memory for storing data related to the received echoes and the locations of the ultrasound transducer adjacent the patient's skin at which the echoes were received, a laser source, and a controller for exciting the ultrasound transducer, for providing the data related to the received echoes and locations to the memory, for converting the received echoes into a laser power necessary to affect the structure to which the stored data relates, and for exciting the laser source at the laser power necessary to affect the structure to which the stored data relates.

2. The apparatus of claim 1 wherein the controller further controls the location of the ultrasound transducer.

3. The apparatus of claim 2 wherein the controller further controls the location of the laser source.

4. The apparatus of claim 1 wherein the controller further controls the location of the laser source.

5. The apparatus of claim 1 further comprising a monitor for observing the location of the ultrasound transducer relative to the patient's skin.

6. The apparatus of claim 1 further comprising a monitor for observing the location of the laser source relative to the patient's skin.

7. The apparatus of claim 2 further comprising a monitor for observing the location of the ultrasound transducer relative to the patient's skin.

8. The apparatus of claim 2 further comprising a monitor for observing the location of the laser source relative to the patient's skin.

9. The apparatus of claim 3 further comprising a monitor for observing the location of the ultrasound transducer relative to the patient's skin.

10. The apparatus of claim 3 further comprising a monitor for observing the location of the laser source relative to the patient's skin.

11. The apparatus of claim 4 further comprising a monitor for observing the location of the ultrasound transducer relative to the patient's skin.

12. The apparatus of claim 4 further comprising a monitor for observing the location of the laser source relative to the patient's skin.

* * * * *